US012377297B2

(12) United States Patent
Sibuet et al.

(10) Patent No.: US 12,377,297 B2
(45) Date of Patent: Aug. 5, 2025

(54) BREATHING EQUIPMENT FOR AN AIRCRAFT, BREATHING ASSEMBLY AND METHOD FOR STOWING THE BREATHING EQUIPMENT

(71) Applicant: SAFRAN AEROTECHNICS, Plaisir (FR)

(72) Inventors: Jean-Philippe Sibuet, Moissy-Cramayel (FR); Alexandre Besson, Moissy-Cramayel (FR)

(73) Assignee: SAFRAN AEROTECHNICS, Plaisir (FR)

( * ) Notice: Subject to any disclaimer, the term of this patent is extended or adjusted under 35 U.S.C. 154(b) by 1023 days.

(21) Appl. No.: 17/431,679

(22) PCT Filed: Feb. 17, 2020

(86) PCT No.: PCT/FR2020/050289
§ 371 (c)(1),
(2) Date: Feb. 14, 2022

(87) PCT Pub. No.: WO2020/169912
PCT Pub. Date: Aug. 27, 2020

(65) Prior Publication Data
US 2022/0193464 A1 Jun. 23, 2022

(30) Foreign Application Priority Data
Feb. 18, 2019 (FR) ........................................ 1901609

(51) Int. Cl.
*A62B 18/08* (2006.01)
*A61F 9/02* (2006.01)
(Continued)

(52) U.S. Cl.
CPC ............ *A62B 18/084* (2013.01); *A61F 9/029* (2013.01); *A62B 9/006* (2013.01); *A62B 25/00* (2013.01); *B64D 11/00* (2013.01)

(58) Field of Classification Search
CPC ....... A62B 18/02; A62B 18/025; A62B 18/04; A62B 18/045; A62B 18/08; A62B 18/06; A62B 18/082; A62B 18/084
See application file for complete search history.

(56) References Cited

U.S. PATENT DOCUMENTS 1,942,442 A * 1/1934 Armand ............... A62B 18/084
2/9
RE20,211 E * 12/1936 Motsinger ............ A62B 18/084
128/207.11
(Continued)

FOREIGN PATENT DOCUMENTS

CA   3008228 A1 * 12/2018 ........... A62B 18/084
CA   3012150 A1 *  1/2019 ............. A62B 18/02
(Continued)

OTHER PUBLICATIONS

First Office Action dated May 7, 2022 in corresponding Chinese application No. 202080023629.1, 10 pages.
(Continued)

*Primary Examiner* — Tu A Vo
(74) *Attorney, Agent, or Firm* — CHRISTENSEN O'CONNOR JOHNSON KINDNESS PLLC

(57) ABSTRACT

A breathing apparatus for aircraft includes a breathing mask with an oronasal face cover and a support. The oronasal face cover has a cavity and the support supports a transparent lens and has an upper edge portion. An inflatable harness extends around the user's head opposite the shell and includes at least one rear portion.
(Continued)

A guiding link includes an upper end linked to the upper edge portion and a lower end, the upper end being linked to the upper edge portion, the lower end being linked to the rear portion of the harness.

A plate is linked to the lower end of the guiding link and has an abutment face that contacts the oronasal face cover, facing the cavity.

12 Claims, 6 Drawing Sheets

(51) Int. Cl.
*A62B 9/00* (2006.01)
*A62B 25/00* (2006.01)
*B64D 11/00* (2006.01)

(56) References Cited

U.S. PATENT DOCUMENTS

| | | | | |
|---|---|---|---|---|
| 2,148,431 | A * | 2/1939 | Brown | A62B 18/084 128/205.27 |
| 2,400,077 | A * | 5/1946 | Dauster | A62B 18/084 2/416 |
| 4,664,108 | A * | 5/1987 | Ansite | A62B 7/08 128/207.11 |
| 5,036,846 | A * | 8/1991 | Aulgur | A62B 18/084 128/205.24 |
| 5,488,948 | A * | 2/1996 | Dubruille | A62B 18/084 2/6.1 |
| 5,623,923 | A * | 4/1997 | Bertheau | A62B 18/084 2/6.1 |
| 5,664,566 | A * | 9/1997 | McDonald | A62B 18/084 128/205.25 |
| 5,941,245 | A * | 8/1999 | Hannah | A62B 18/084 128/207.11 |
| 5,954,052 | A * | 9/1999 | McDonald | B64D 10/00 206/485 |
| 5,957,132 | A | 9/1999 | McDonald et al. | |
| 6,039,045 | A * | 3/2000 | Bertheau | A62B 18/084 128/207.11 |
| 6,470,887 | B1 * | 10/2002 | Martinez | A62B 18/084 128/207.11 |
| 10,695,591 | B2 * | 6/2020 | Sibuet | B64D 25/00 |
| 2002/0020652 | A1 * | 2/2002 | Martinez | B64D 10/00 128/205.25 |
| 2002/0157668 | A1 * | 10/2002 | Bardel | A62B 17/04 128/205.25 |
| 2002/0189617 | A1 * | 12/2002 | Cordero | B64D 10/00 128/205.25 |
| 2003/0000530 | A1 * | 1/2003 | McDonald | A62B 18/08 128/205.25 |
| 2003/0002164 | A1 * | 1/2003 | McDonald | B64D 10/00 359/630 |
| 2005/0210556 | A1 * | 9/2005 | Martinez | A62B 18/082 2/9 |
| 2009/0145436 | A1 * | 6/2009 | Aubonnet | A62B 18/084 128/204.29 |
| 2014/0290665 | A1 * | 10/2014 | Libis | B64D 10/00 128/206.27 |
| 2016/0228732 | A1 * | 8/2016 | Cooper | A62B 18/02 |
| 2016/0375275 | A1 * | 12/2016 | Cooper | A62B 9/04 128/205.25 |
| 2018/0361179 | A1 * | 12/2018 | Sibuet | A62B 27/00 |
| 2019/0022434 | A1 | 1/2019 | Sibuet et al. | |

FOREIGN PATENT DOCUMENTS

| | | | | |
|---|---|---|---|---|
| EP | 1486233 | A1 * | 12/2004 | A62B 18/08 |
| FR | 2752165 | A1 * | 2/1998 | A62B 18/084 |
| FR | 2784900 | A1 * | 4/2000 | A62B 18/084 |
| WO | WO-9704837 | A1 * | 2/1997 | A41D 13/1176 |
| WO | WO-2012066394 | A2 * | 5/2012 | A62B 18/084 |
| WO | WO-2012085616 | A1 * | 6/2012 | A62B 25/00 |
| WO | WO-2013064856 | A1 * | 5/2013 | A62B 18/02 |
| WO | WO-2019008446 | A1 * | 1/2019 | A62B 18/02 |

OTHER PUBLICATIONS

International Search Report mailed May 26, 2020, issued in corresponding International Application No. PCT/FR2020/050289, filed Feb. 17, 2020, 5 pages.

Written Opinion mailed May 26, 2020, issued in corresponding International Application No. PCT/FR2020/050289, filed Feb. 17, 2020, 7 pages.

English translation of Written Opinion mailed May 26, 2020, issued in corresponding International Application No. PCT/FR2020/050289, filed Feb. 17, 2020, 7 pages.

International Preliminary Report on Patentability mailed Aug. 10, 2021, issued in corresponding International Application No. PCT/FR2020/050289, filed Feb. 17, 2020, 8 pages.

* cited by examiner

BREATHING EQUIPMENT FOR AN AIRCRAFT, BREATHING ASSEMBLY AND METHOD FOR STOWING THE BREATHING EQUIPMENT

FIELD OF THE INVENTION

The invention relates to a breathing apparatus for aircraft, a breathing unit and a method for stowing a breathing apparatus in an aircraft. More specifically, said breathing unit is of the type essentially comprising a breathing apparatus provided with an inflatable harness and a stowage box.

In particular, the breathing apparatus comprises a breathing mask including a shell. The shell has an overall cavity, the shell being able to comprise an oronasal face cover having a first cavity and a support for a transparent lens forming an assembly usually referred to as a bezel, and having a second cavity.

STATE OF THE ART

The breathing apparatus normally used by aircraft crew members must be placed securely and quickly on the pilot's head as a precautionary measure or in an emergency situation. This should be a one-handed operation, as the other hand is often required for other essential tasks.

For example, due to a pressurisation failure or another technical problem that causes the aircraft cabin to depressurise, due to the presence of smoke and/or toxic gas, or more generally in an emergency situation, the pilot of an aircraft must quickly put on their breathing apparatus to provide them with the oxygen they need to breathe, and they often have to do this with one hand while their other hand is busy controlling the aircraft. Thus, the use of an inflatable head harness has been suggested to allow the breathing apparatus to be put on with one hand. Generally, the head harness is formed by one or more longitudinally elastically stretchable tube rings. The harness is substantially dome-shaped or ring-shaped and is diametrically expanded by the injection of pressurised gas in order to cause the harness to increase in size so that it can be positioned on a user's head. The flow of gas is controlled by a valve attached to the breathing apparatus and, after the harness has been enlarged, the breathing apparatus is placed in contact with the user's face with the harness extended and spaced apart from the back of the head. Once the breathing apparatus has been correctly positioned, the pressure in the harness is released, causing the harness to spring back and come into contact with the pilot's head (gripping it lightly), so that the breathing apparatus is held in its correct position. During this time, the pilot's other hand is free to control the aircraft or perform other tasks that may be required.

Since the space for stowing the breathing apparatus is generally limited in an aircraft, it is not easy to stow the breathing apparatus in a stowage box in an appropriate manner. However, an incorrect stowage position of the breathing apparatus may prevent correct deployment of the harness during inflation.

In particular, when the breathing apparatus is stowed in a stowage device, the harness should be outside the (one or more) cavity (ies). Thus, the risk of having a fold of the harness inserted into (one of) the shell cavity (ies) when the harness starts to inflate is reduced, so that the risk of a harness inflation problem is reduced.

An active system, with a releasable link between the harness and the stowage box, is already known from document US2018/0361179A1. The releasable link forces the extraction of the harness, while controlling the opening of the oxygen supply. This system requires a modification not only of the breathing apparatus, but also of the stowage box.

Also known from US2019/022434A1 is a "semi-active" system in which a strap on the harness is used for stowage. A special tip at the end of this strap interfaces with the doors of the box. If the tip is correctly positioned, the doors can be closed. If the tip is not correctly positioned, and the harness is not correctly stowed, the doors do not close, indicating that the stowage is unsatisfactory and should be redone.

The invention proposes a breathing apparatus with improved ergonomics to facilitate correct stowage.

DISCLOSURE OF THE INVENTION

The breathing apparatus is intended to supply a respiratory gas to a user and includes:
- a breathing mask comprising a shell, the shell has a cavity and is configured for contacting the user's head around the user's mouth and nose, the shell supporting a transparent lens and comprising an upper edge portion extending above the transparent lens,
- an inflatable harness configured for extending around the user's head opposite the shell in order to hold the shell against the user's face, the harness comprising at least one rear portion intended to be placed facing a rear (occipital) portion of the user's head,
- a guiding link having an upper end and a lower end, the upper end being linked to the upper edge portion, and
- a plate linked to the lower end of the guiding link and having a bearing face configured for contacting the shell, facing the cavity, the plate being linked to the rear portion of the harness.

The plate and the guiding link make it possible to position the rear portion of the harness and to prevent it from being inserted into the (one or more) cavity (ies) of the breathing mask. Thus, there is no need to modify the stowage box to improve the stowage of the breathing apparatus in the stowage box. Additionally, existing breathing apparatuses can be easily modified to improve their stowage position.

Of course, increasing the size of the plate tends to reduce the risk of the harness entering the cavity. However, the larger the plate, the more difficult it is to stow the breathing apparatus in the stowage box and to remove it quickly without damaging it. A compromise is therefore necessary.

According to an additional aspect, the guiding link preferably has a torsional flexibility of less than half a turn. This reduces the risk of twisting the harness and of incorrectly stowing the breathing apparatus.

According to another aspect, the guiding link is preferably elongate and flat. This reduces the size of the guiding link when the breathing mask is in the stowed position and reduces the risk of incorrect stowage of the breathing apparatus.

According to another aspect, the guiding link preferably has an upper portion and a lower portion, the guiding link being configured for being folded with the upper portion on the plate and the lower portion between the upper portion and the plate. This allows for better control of the positioning of the guiding link when the breathing mask is in the stowed position.

According to a complementary aspect, the upper portion is preferably rigid. This allows for even better control of the positioning of the guiding link when the breathing mask is in the stowed position. Rigid should be understood to mean that the guiding link does not bend under its own weight and the weight of the harness.

According to a further complementary aspect, the first portion preferably has a length greater than or equal to 10 centimeters, more preferably greater than or equal to 15 centimeters. In this way, the positioning of the upper portion of the guiding link is better controlled and the guiding link more effectively opposes the presence of a portion of the harness in the cavity.

According to another aspect, the upper portion preferably comprises two arms extending longitudinally and transversely (perpendicularly to the direction in which the arms extend) spaced apart from one another by a distance greater than or equal to 3 centimeters, more preferably greater than or equal to 5 centimeters, and the breathing apparatus comprises two lower portions extending between the upper portion and the plate, i.e. the upper portion being connected to the plate via the lower portion.

According to another aspect, the first portion is rotatably mounted on the upper edge portion. In this way, the positioning of the guiding link is well controlled in the stowage position and its positioning adapts to the user's morphology.

According to another aspect, the lower portion is at least partly flexible and arranged between the upper portion and the plate. This allows the guiding link to be easily adjusted when deploying the harness, when placing the breathing apparatus in the stowed position and according to the user's morphology. Flexible should be understood to mean that the lower portion bends under its own weight and the weight of the harness.

According to another aspect, the lower portion preferably comprises at least one rigid element. In this way, the twisting of the lower portion is reduced, while still allowing the lower portion to be folded.

According to a complementary aspect, the second portion preferably comprises a series of rigid elements hingedly connected to one another. This allows the lower portion to bend at multiple points located between the rigid elements.

According to another aspect, the lower portion preferably comprises a strap, the strap extending beyond the lower end forming a loop around a tube of the harness and the loop has ends held on the plate. Thus, the strap also serves to attach the plate to the harness.

According to an alternative aspect, the lower end of the guiding link is preferably linked to the rear portion of the harness via the plate.

According to another aspect, the breathing apparatus is preferably additionally provided with a sign for correct positioning in a stowage position. This makes it easier to place the breathing apparatus in a satisfactory stowed position and reduces the risk of the user placing the breathing apparatus in an incorrect stowed position.

According to another aspect, the shell preferably comprises an oronasal face cover and a support, the oronasal face cover having a first cavity and being configured for contacting the user's head around the user's mouth and nose, the support supporting a transparent lens and having a second cavity.

The invention also relates to a breathing unit comprising the above-mentioned breathing apparatus and a stowage box including a housing configured for receiving the breathing apparatus in a stowage position, said stowage box having an opening for access to the housing.

The invention additionally proposes a method for stowing the breathing apparatus in the stowage box of the above-mentioned breathing unit, the method comprising:

a) moving the plate to be in contact with the oronasal face cover, b) pivoting the guiding link near its upper end with respect to the breathing mask, c) placing the breathing apparatus in a stowed position by folding the guiding link so that the upper portion of the guiding link, the lower portion of the guiding link and the plate overlap; and d) inserting the breathing apparatus into the stowage box.

BRIEF DESCRIPTION OF THE FIGURES

Further features and advantages will become apparent from the following detailed description, made in relation to the annexed drawings in which.

DETAILED DESCRIPTION

Figure 1:
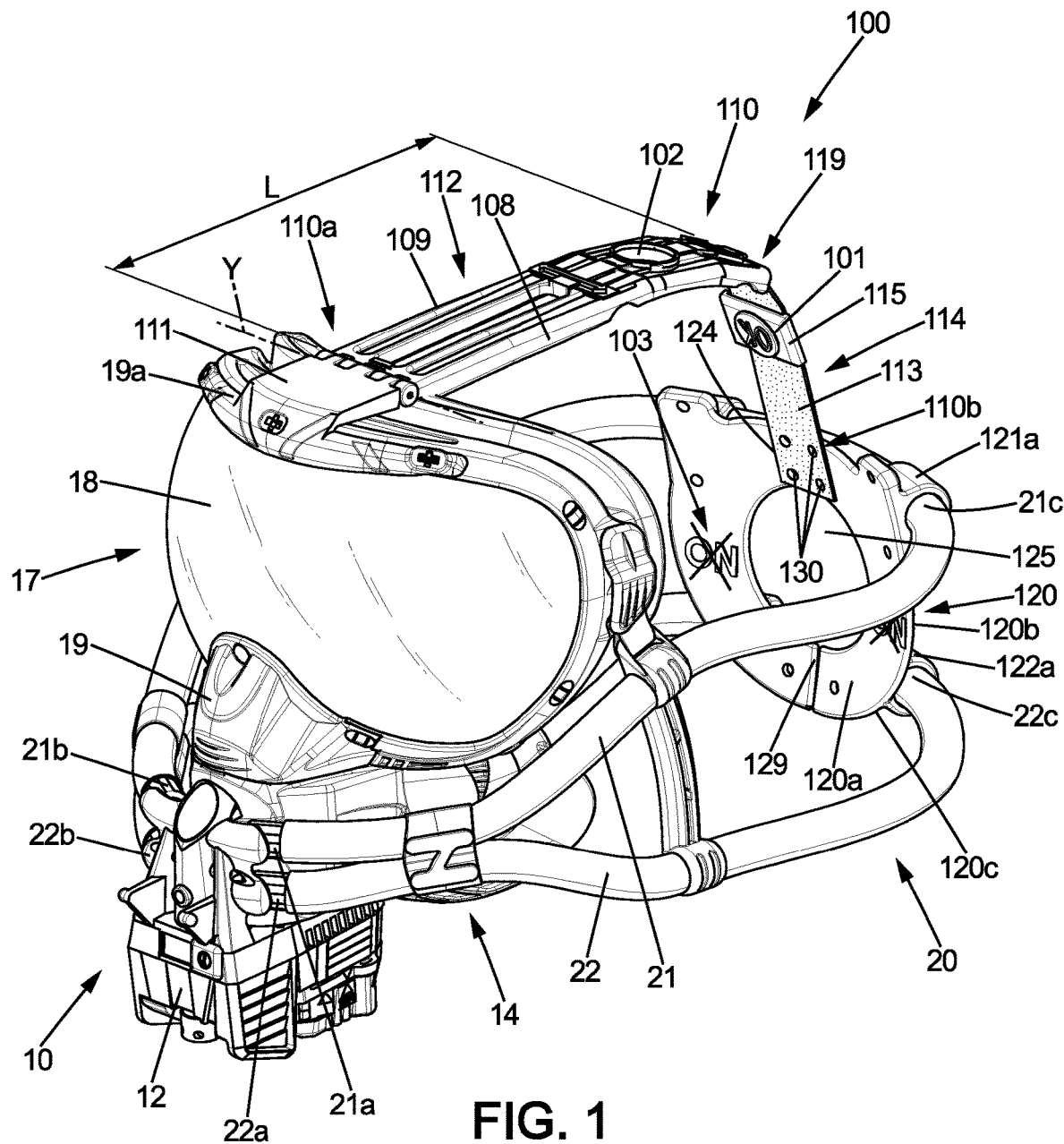
FIG. 1 depicts a breathing apparatus, in a front perspective, in an operational position.

The figures show a breathing unit 1 comprising a breathing apparatus 100 and a stowage box 30. The breathing apparatus 100 is intended to be installed in an aircraft and to supply respiratory gas to a user in an emergency situation or for preventative purposes. The breathing apparatus 100 essentially includes a breathing mask 10, an inflatable harness 20, a guiding link 110 and an occipital plate 120.

The breathing mask 10 comprises a shell. In the shown embodiment, the shell comprises an oronasal face cover 14 and a support 17. The oronasal face cover 14 has a first cavity 13 and a seal 16 extending around the first cavity 13 and configured for contacting the user's head around the user's mouth and nose. The support 17 comprises a transparent lens 18. The support 17 has a second cavity 15. The support 17 has a seal 11 extending around the second cavity and intended for contacting the user's head around the eyes. The support 17 comprises a contour 19 extending around the transparent lens 18. The contour 19 has an upper edge portion 19a extending above the transparent lens 18.

In the shown embodiment, the support 17 is removable from the oronasal face cover 14 and forms a removable bezel. The first cavity 13 can be isolated from the second cavity 15, particularly when the support 17 is separated from the oronasal face cover. Alternatively, the support 17 cannot be released from the oronasal face cover 14 and, in this case, the first cavity 13 and the second cavity 15 may not be detached and form two areas of a single overall cavity. Such a breathing mask is usually referred to as a full-face mask.

The breathing mask 10 additionally comprises a gripping housing 12. The gripping housing 12 contains an on-demand regulator (not shown) which supplies the first cavity 13 with a breathing mixture comprising a respiratory gas and ambient air. A supply tube 2 is attached to the gripping housing 12. The supply tube 2 is connected upstream to a pressurised source of respiratory gas (not shown) preferably containing at least 95% oxygen and downstream to the on-demand regulator in order to supply the on-demand regulator with respiratory gas.

The harness 20 is configured for extending around the user's head opposite the shell in order to hold the shell in contact with the user's head, the harness 20 comprising a rear portion 25 intended to be placed facing the rear (occipital) portion of the user's head. In the shown embodiment, the harness 20 comprises an upper tube 21 and a longitudinally elastically extensible lower tube 22. The upper tube 21 extends continuously between a first upper end 21a and a second upper end 21b held on the gripping housing 12. The lower tube 22 extends continuously between a first lower end 22a and a second lower end 22b held on the gripping housing 12.

The upper tube 21 is connected by at least one of the first upper end 21a and the second upper end 21b to a source of pressurised gas via an inflation valve (not shown) making it possible selectively to inject the pressurised gas into the upper tube 21 (so as to increase the length of the upper tube 21) or to discharge the pressurised gas (so as to contract the upper tube 21) by springing back. The lower tube 22 is connected by at least one of the first lower end 22a and the second lower end 22b to the source of pressurised gas via an inflation valve (not shown) making it possible selectively to inject the pressurised gas into the lower tube 22 (so as to increase the length of the lower tube 22) or to discharge the pressurised gas (so as to contract the lower tube 22) by springing back. In the shown embodiment, the source of pressurised gas consists of the source of respiratory gas.

Alternatively, the upper tube 21 and the lower tube 22 may be replaced by two side tubes connected to one another, preferably by the occipital plate 120, the two side tubes then being connected to the gripping housing for one substantially at the first lower end and the first upper end (or contour 19) and for the other substantially at the second lower end and the second upper end (or contour 19). Such an alternative harness is well known.

The guiding link 110 has an upper end 110a and a lower end 110b. The upper end 110a is linked to the upper edge portion 19a via a linking member 111 attached to the upper edge 19a. The lower end 110b is linked to the rear portion 25 of the harness 20.

The occipital plate 120 has an inner face 120a and an outer face 120b. The inner face 120a is configured for contacting the oronasal face cover 14, facing the first cavity 13 in a stowage position of the breathing apparatus. The occipital plate 120 has a contour 120c corresponding to the contour of the seal 16 of the oronasal face cover 14 against which it presses in the stowage position (see in particular FIG. 5), in order to guide the operator when positioning the occipital plate 120. The lower end 110b of the guiding link 110 is linked to the occipital plate 120. In the shown embodiment, four clips 130 are provided for attaching the lower end 110b of the guiding link to the occipital plate 120. Preferably, the lower end 110b of the guiding link 110 is attached to the inner face 120a of the occipital plate 120. In the shown embodiment, a groove-like recess 124 is provided in the inner face 120a of the occipital plate 120, so that the bottom end 110b of the guiding link 110 is embedded in the recess.

The occipital plate 120 is provided with holding members forming tube passages. In the shown embodiment, the occipital plate comprises a first upper holding member 121a, a second upper holding member 121b, a first lower holding member 122a and a second lower holding member 122b. The first upper holding member 121a, the second upper holding member 121b, the first lower holding member 122a and the second lower holding member 122b project from the outer face 120b of the occipital plate 120. The first upper holding member 121a has a bore receiving a first upper intermediate portion 21c of the upper tube 21. The second upper holding member 121b has a bore receiving a second upper intermediate portion 21d of the upper tube 21. The first lower holding member 122a has a bore receiving a first lower intermediate portion 22c of the lower tube 22. The second lower holding member 122b has a bore receiving a second lower intermediate portion 22d of the lower tube 22.

The upper tube 21 comprises an upper rear portion 21e extending between the first upper intermediate portion 21c and the second upper intermediate portion 21d. The lower tube 22 comprises a lower rear portion 22e extending between the first lower intermediate portion 21c and the second lower intermediate portion 21d.

In the shown embodiment, the rear portion 25 of the harness 20 comprises the first upper intermediate portion 21c, the upper rear portion 21e, the second upper intermediate portion 21d, the first lower intermediate portion 22c, the lower rear portion 22e and the second lower intermediate portion 22d.

Alternatively, the upper rear portion 21e and/or the lower rear portion 22e could be omitted. Thus, the upper tube 21 (and the lower tube 22, respectively) appears to comprise two separate portions connected by the occipital plate 120, one of the separate portions extending between the first upper end 21a (and the first lower end 22a, respectively) and the first upper intermediate portion 21c (and the first lower intermediate portion 22c, respectively) forming the end, the other of the separate portions extending between the second upper end 21b (and the second lower end 22b, respectively) and the second upper intermediate portion 21d (and the second lower intermediate portion 22d, respectively) forming the end.

According to another alternative embodiment, the occipital plate 20 may comprise a single upper holding member instead of the first upper holding member 121a and the second upper holding member 121b and/or a single lower holding member instead of the first lower holding member 122a and the second lower holding member 122b.

The occipital plate 120 thus connecting the upper tube 21 to the lower tube 22 makes it possible to maintain the spacing between the upper tube 21 and the lower tube 22 in the rear portion 25 of the harness and replaces the spacers that usually extend between the upper tube and the lower tube of the harness.

The occipital plate 120 is rigid enough to prevent it from being forced into the first cavity 13 of the oronasal face cover 14. However, the inner face 120a of the occipital plate 120 must be flexible enough to avoid hitting the back of the user's head. In particular, to avoid causing pain at the occipital region of the user's head, the plate 120 has a central hole 125. Additionally, the inner face 120a of the plate is preferably at least partially covered with a flexible material.

The guiding link 110 comprises an upper portion 112 and a lower portion 114. The upper portion 112 is connected at the upper end 110a to the upper edge 19a of the support 17 via the linking member 111. The upper portion 112 is rotatably mounted on the linking member 111 about a hinge axis Y extending in a transverse direction, i.e. substantially along the upper edge 19a. The lower portion 114 forms a flexible, non-elastic link. The lower portion 114 is attached to the upper portion 112, by rivets, bolts or other mechanical fasteners, at a junction area 119. The upper portion 112 extends from the upper end 110a to the junction area 119.

The lower portion 114 extends as a continuation of the upper portion 112 from the junction area 119 to the lower end 110b. The lower portion 114 connects the upper portion 112 to the occipital plate 120. The upper portion 112 is preferably made of a material having moderate hardness, preferably a shore hardness of at least 90 and/or of silicone.

The guiding link 100 makes it possible to reduce the risk of the occipital plate 120 being stowed too high with respect to the breathing mask 10 and abutting against the support 17 during the inflation of the harness 20, which would increase the time required to inflate the harness 20, or even cause unsatisfactory deployment of the harness 20 during inflation.

Figure 2:
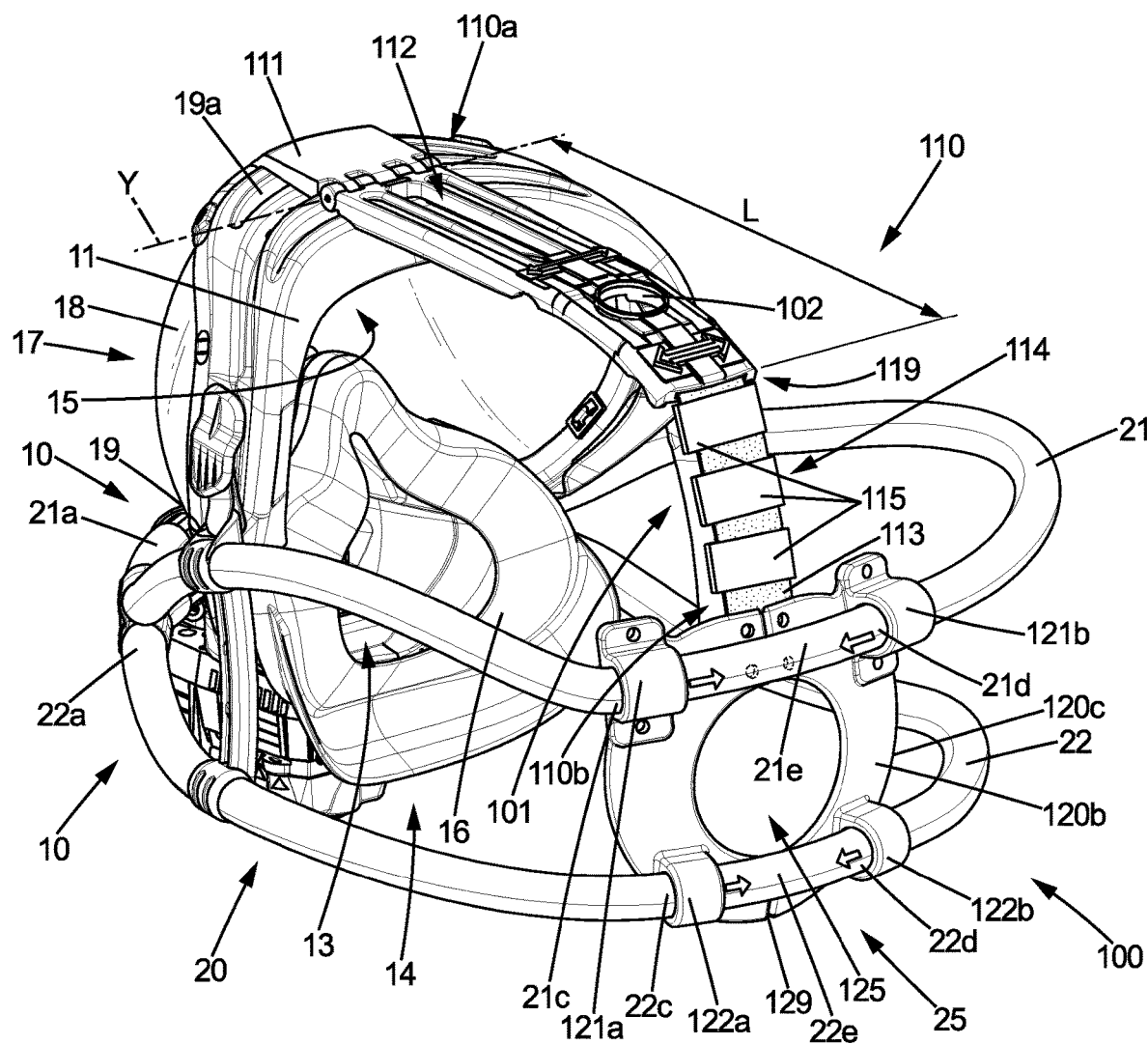
FIG. 2 depicts the breathing apparatus, in a rear perspective, in the operational position, according to a first alternative embodiment.

In the operational position of the breathing apparatus 100, shown in FIGS. 1 and 2, the breathing apparatus is intended to be positioned on the head of a user (not shown) with the harness 20 unfolded but not inflated, with the upper portion 112 extending substantially horizontally around the user's head. In the embodiment shown in FIGS. 1 and 2, the upper portion 112 of the guiding link 110 curves gradually in the vicinity of the junction area 119, in order to better follow the shape of the head. The lower portion 114 then has a curved shape extending essentially over the back of the user's head. The lower portion 114 extends substantially vertically behind the user's head in the vicinity of the lower end 110b and partly over the top of the head substantially horizontally in the vicinity of the junction area 119. Alternatively, the upper portion 112 may be entirely flat (from the upper end 110a to the junction area 119, as shown in FIG. 3).

Figure 3:
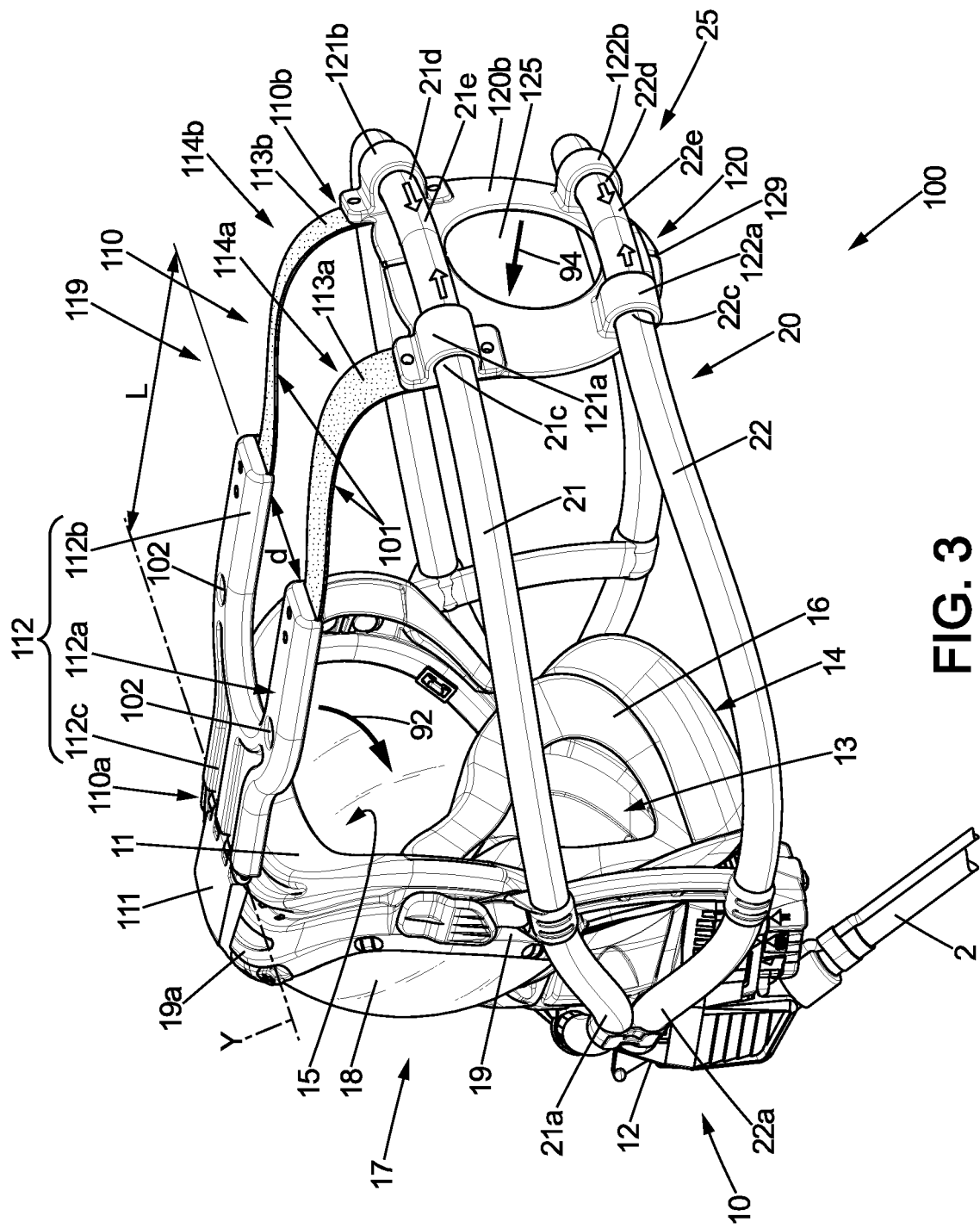
FIG. 3 depicts the breathing apparatus, in a rear perspective, in a fitting position, according to a second alternative embodiment.

In the fitting position of the breathing apparatus, shown in FIG. 3, the harness 20 is deployed, inflated. The upper portion 112 of the guiding link 110 is substantially in the same position as in the operational position of the breathing apparatus 100. In contrast, the shape of the lower portion 114 of the guiding link 110 is changed when the harness 20 is inflated (conversely when the harness 20 is deflated), with the lower portion 114 of the guiding link 110 extending substantially horizontally when the harness 20 is inflated, with the lower portion 114 of the guiding link 110 extending substantially vertically only in the immediate vicinity of the lower end 110b. Because the lower portion 114 is at least partially flexible, the lower portion 114 readily adapts to the movement of the rear portion 25 of the harness 20 opposite (away from) the breathing mask 10 during inflation (inducing elongation) of the first tube 21 and the second tube 22.

Figure 5:
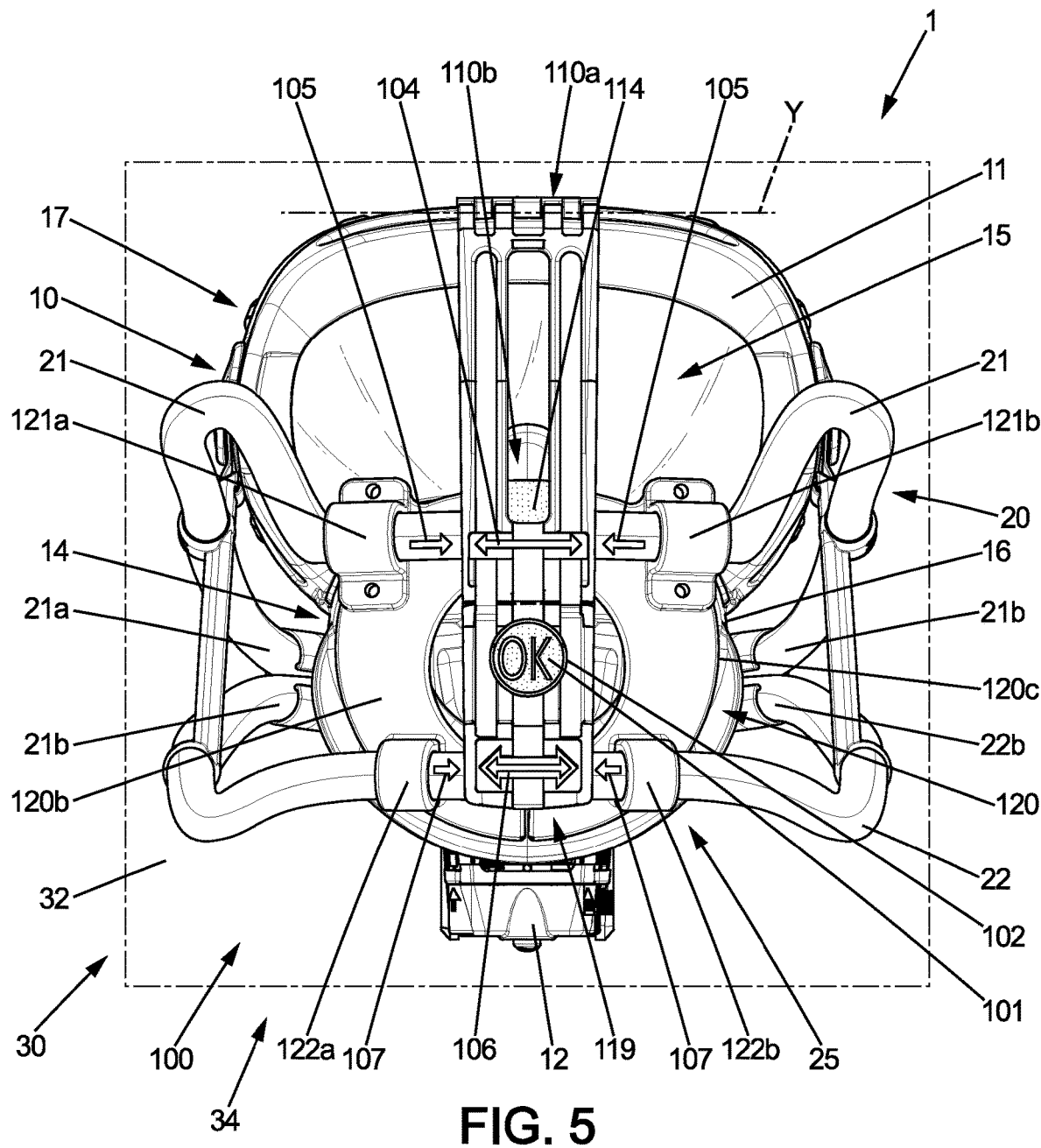
FIG. 5 depicts the breathing apparatus, in a stowage position, inserted into a stowage box.

In the stowage position of the breathing apparatus 110, shown in FIG. 5, the occipital plate 120 bears against the shell. Specifically, the occipital plate bears on the oronasal face cover 14. Preferably concomitantly with the occipital plate 120 being brought closer to the oronasal face cover 14 as indicated schematically by the arrow 92 in FIG. 3, the user pivots the upper portion 112 of the guiding link 110 relative to the breathing mask 10 by rotation about the hinge axis Y by approximately 90 degrees, as indicated schematically by the arrow 94 in FIG. 3, until the upper portion 112 of the guiding link 110 bears on the occipital plate 120.

In the stowed position, the lower portion 114 is folded (180 degrees) close to the junction area 19 and close to the lower end 110b. The lower portion 114 extends between the upper portion 112 and the occipital plate 120 between these two folds. In the embodiment shown in FIGS. 1 and 2, the upper portion 112 has two side flanges 108, 109 between which the lower portion 114 is held in the stowage position.

The upper portion 112 has a length L (see in particular FIGS. 1 to 3), perpendicular to the hinge axis Y, of at least 10 centimeters, preferably at least 15 centimeters and more preferably about 17 centimeters, to prevent the free end of the upper portion from becoming wedged in the lower portion of the seal 16 of the oronasal face cover 14.

The breathing apparatus is also provided with a sign for correct positioning in the stowed position. Thus, the lower portion 114 of the guiding link 110 is additionally provided with a correct position indicator 101, consisting in the embodiment of a green marker and preferably of an "OK" indication, while the upper portion 112 of the guiding link 110 comprises a viewing hole 102. As shown in FIG. 5, when the breathing apparatus 110 is in a satisfactory stowed position, the correct position indicator 101 is facing the viewing hole 102 of the upper portion 102 and is therefore visible to the user. If the occipital plate 120 is incorrectly positioned, the lower portion 114 is offset with respect to the upper portion 112 of the guiding link 110, in particular the correct position indicator 101 is no longer facing the viewing hole 102. Since the correct position indicator is behind the upper portion 112 of the guiding link 110, the correct position indicator is not visible.

Figure 6:
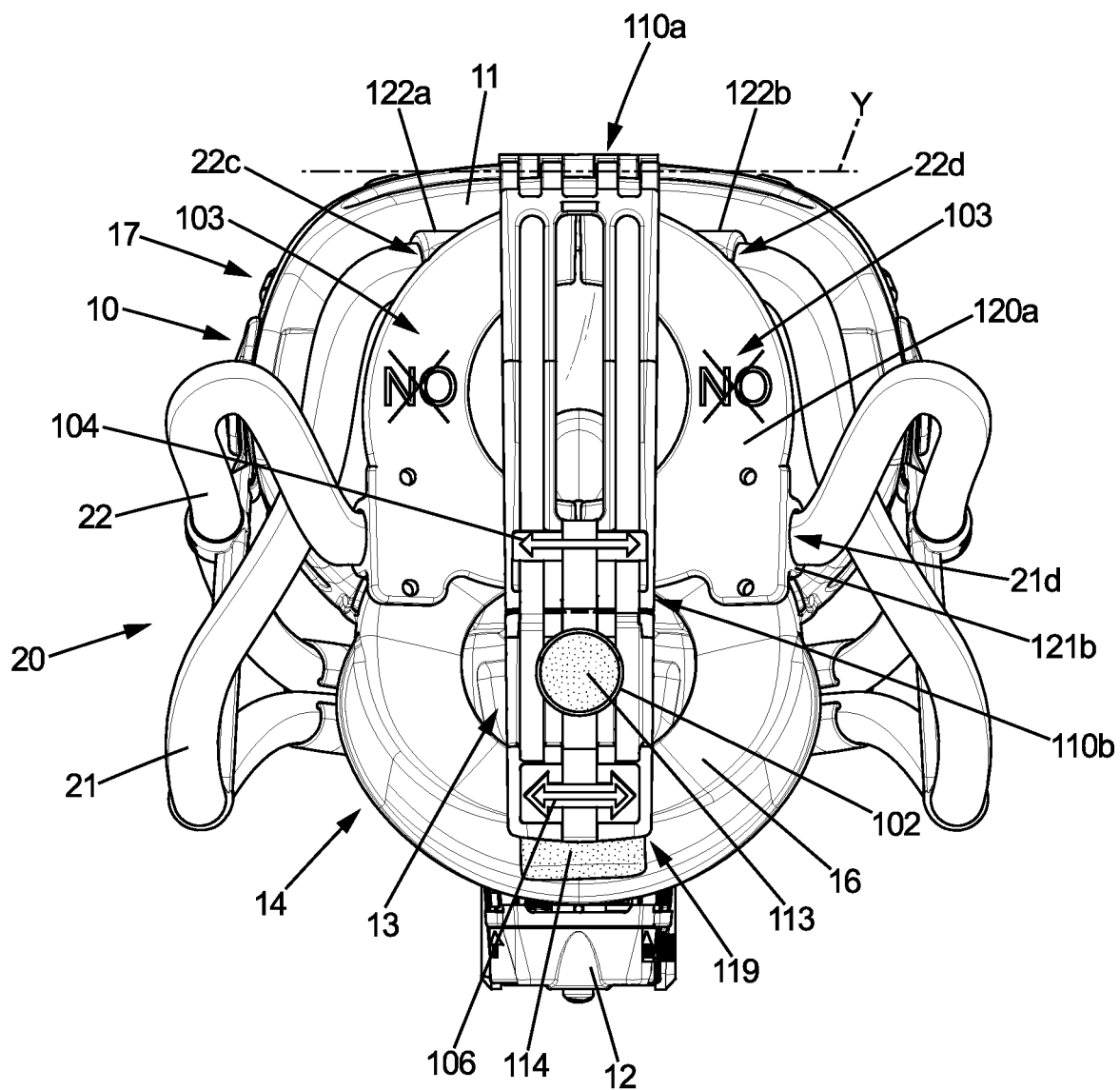
FIG. 6 depicts the breathing apparatus in a position not suitable for stowage.

Thus, the occipital plate 120 is provided with a visual marker indicating to the operator whether the occipital plate 120 is correctly positioned in the stowage position, primarily to prevent the plate from turning over by 180° regardless of the direction of turning. Additionally, as shown in FIG. 6, the breathing apparatus 110 has an incorrect position indicator 103. In the shown embodiment, the incorrect position indicator 103 consists of "NO" indications or equivalent pictographs (not shown) supported by the inner face 120a of the occipital plate 120, preferably with a hazard-related sign, such as the colour red and/or a triangle, or a cross symbolising that the occipital plate 120 is not positioned on the correct side. As this incorrect position indicator 103 is supported by the inner face 120a of the occipital plate 120, it is only visible to the user in the stowed position if the occipital plate 120 is positioned, turned 180 degrees (top to bottom or even sideways), indicating incorrect stowage of the harness 20. Indeed, the inner face 120a is intended to face the shell 14, 17 and to come into contact with the shell when the breathing apparatus 100 is in the correct stowage position, in particular bearing on the oronasal face cover 14 in the shown embodiment. In the configuration shown in FIG. 6, the inner face 120a is turned away from the breathing mask 10, resulting in the harness 20 being incorrectly positioned, and then is visible to the user.

Additionally, the upper portion 112 of the guiding link 110 and the occipital plate 120 are provided with markings (arrows in the shown embodiment, preferably white or green) that guide the user towards the correct alignment and position. More specifically, the upper portion 112 of the guiding link 110 has a first marker 104 for positioning the upper tube 21 and a second marker 106 for positioning the lower tube 22. The first marker 104 and the second marker 106 are double arrows in the shown embodiment. The upper tube 21 has upper indicators 105 of the position of the upper tube 21 and the lower tube 22 has lower indicators 107 of the position of the lower tube 22. The upper indicators 105 of the position of the upper tube 21 and the lower indicators 107 of the position of the lower tube 22 are arrows in the shown embodiment. When the breathing unit 110 is in the correct stowage position, as shown in FIG. 5, the upper indicators 105 of the position of the upper tube 21 are located on either side of the first marker 104 and at the same level as the first marker 104, so that the upper indicators 105 of the position of the upper tube 21 and the first marker 104 are aligned. Additionally, the lower indicators 107 of the position of the lower tube 107 are located on either side of the second marker 106 and at the same level as the second marker 106, so that the lower indicators 107 of the position of the lower tube 107 and the second marker 106 are aligned.

The stowage box 30 includes a housing 32 and an opening 34 to access the housing 32. When the breathing apparatus 100 is in the correct stowage position, the user inserts the breathing apparatus 100 into the housing 32 through the opening 34 of the stowage box 30, holding the breathing apparatus 100 by the gripping housing 12. Doors may be provided to at least partially close the opening 34, while allowing the gripping housing 12 to be grasped.

When the user wishes to place the breathing apparatus 110 on their head, they grasp the breathing apparatus 100 by the gripping housing 12. Then, they pull on the gripping housing 12 to remove the breathing apparatus 100 from the housing 32 of the stowage box 30, they actuate a control that acts on the inflation valve to inflate the upper tube 21 and the lower tube 22 of the harness 20. The harness 20 deploys in a fraction of a second. The user places the breathing apparatus 100 over their head and then lowers the breathing apparatus 100 around their head. Finally, the user releases the control acting on the inflation valve, the upper tube 21 and the lower tube 22 deflate, the harness 20 contracts and the breathing mask 10 presses against the user's face, while the occipital plate 120 presses against the back of the user's head.

Springs may be arranged between the linking member 111 and the upper portion 112 of the guiding link, so as to urge the upper portion 112 of the guiding link 110 to rise to a substantially horizontal position (perpendicular to the support 17), upon inflation of the harness 20 causing it to deploy from the stowed position. In order to gain flexibility and optimise the overall thickness during stowage, the occipital plate 120 is preferably formed as two portions, referred to as the left portion 126 and the right portion 128, juxtaposed in the transverse direction. The two portions can be connected by a joining element 129 comprising in particular a hinge or a flexible overmolded element (silicone, strap, leaf spring). The amplitude of rotation between the left portion 126 and the right portion 128 is preferably less than 30 degrees (preferably around 20 degrees) in both directions, i.e. a maximum of 60 degrees, preferably 40 degrees, in order to prevent the left portion 126 and the right portion 128 from being folded and the occipital plate 120 from being inserted into the first cavity 13 of the oronasal face cover 14 or the second cavity 15 of the support 17.

This bending between the left portion 126 and the right portion 128 of the occipital plate 120 improves comfort for the user by closely following the curvature of the user's skull.

In the shown embodiments, the upper portion 112 and the lower portion 114 of the guiding link 110 have an elongate, flat shape. Additionally, the lower portion 114 advantageously comprises a strap 113.

In the embodiment shown in FIG. 1, the lower portion 114 of the guiding link 110 additionally comprises a rigid pad 115. The pad 115 is preferably attached to the strap 113. The pad 115 limits the possibility of the lower portion 114 of the guiding link 110 twisting, thus reducing the risk of incorrectly positioning the occipital plate 20 by turning it 180 degrees by twisting the lower portion 114 of the guiding link 110. The twisting of the lower portion 114 of the guiding link 110 is limited by the rigid pad 115, which only allows the strap 113 to be twisted when it is separated from the pad 115, without limiting the bending of the strap 113 when it is separated from the pad 115, so that by correctly positioning the pad (separated from the areas where the lower portion 114 is to be folded) the pad 115 does not interfere with the bending necessary for the guiding link 110 to adapt to the passage of the breathing apparatus 100 from the operational position to the stowage position or vice versa. The correct position indicator 101 is preferably supported by the pad 115.

The alternative embodiment shown in FIG. 2 differs substantially from the embodiment shown in FIG. 1 in that the lower portion 114 of the guiding link 110 comprises three rigid pads 115 distributed over the strap 113. Only the rigid pad 115 arranged between the other two has the correct position indicator 101. In another alternative embodiment (not shown), the lower portion 114 of the guiding link 110 comprises five rigid pads 115. Advantageously, the lower portion 114 of the guiding link 110 comprises between one and five rigid pads 115, only one of which has the correct position indicator 101 since the correct position is unique. The rigid pads 115 are preferably overmolded onto the strap 113 or attached by clipping, riveting, bolting or other suitable attachment means. The number and shape of the pads is configured for avoiding the risk of causing pain to the user due to contact with the user's skull.

The alternative embodiment shown in FIG. 3 differs essentially from the embodiment shown in FIG. 1 in that the lower portion 114 of the guiding link 110 is not provided with a rigid pad, so that the correct position indicator is supported directly by the strap 113.

The alternative embodiment shown in FIG. 3 additionally differs substantially from the embodiment shown in FIG. 1 (and independently of the number of pads 115 that the lower portion 114 of the guiding link 110 comprises) in that the upper portion 112 of the guiding link 100 comprises a first arm 112a and a second arm 112b at the junction area 119 and the guiding link 110 comprises a first lower portion 114a and a separate second lower portion 114b, connecting the upper portion 112 to the occipital plate 120. The first arm 112a is separated from the second arm 112b by a distance d greater than or equal to 3 centimeters, preferably at least equal to 5 centimeters. The first lower portion 114a comprises a first strap 113a and the second lower portion 114b comprises a second strap 113b. This makes it easier to correctly position the breathing apparatus in the stowed position and to ensure the compactness of the breathing apparatus in the stowed position. Additionally, it allows a ponytail or a bun to pass through it.

In the embodiment shown in FIG. 3, the upper portion 112 additionally comprises a base 112c extending from the upper end 110a, the base 112c being connected opposite the upper end 110a to the first arm 112a and to the second arm 112b. The upper portion 112 is thus hingedly connected with respect to the linking member 111 by the base 112c.

Alternatively, the upper portion 112 may be without the base 112c, each of the first arm 112a and the second arm 112b extending to the upper end 110a and being directly hinged to the linking member 111.

Figure 4:
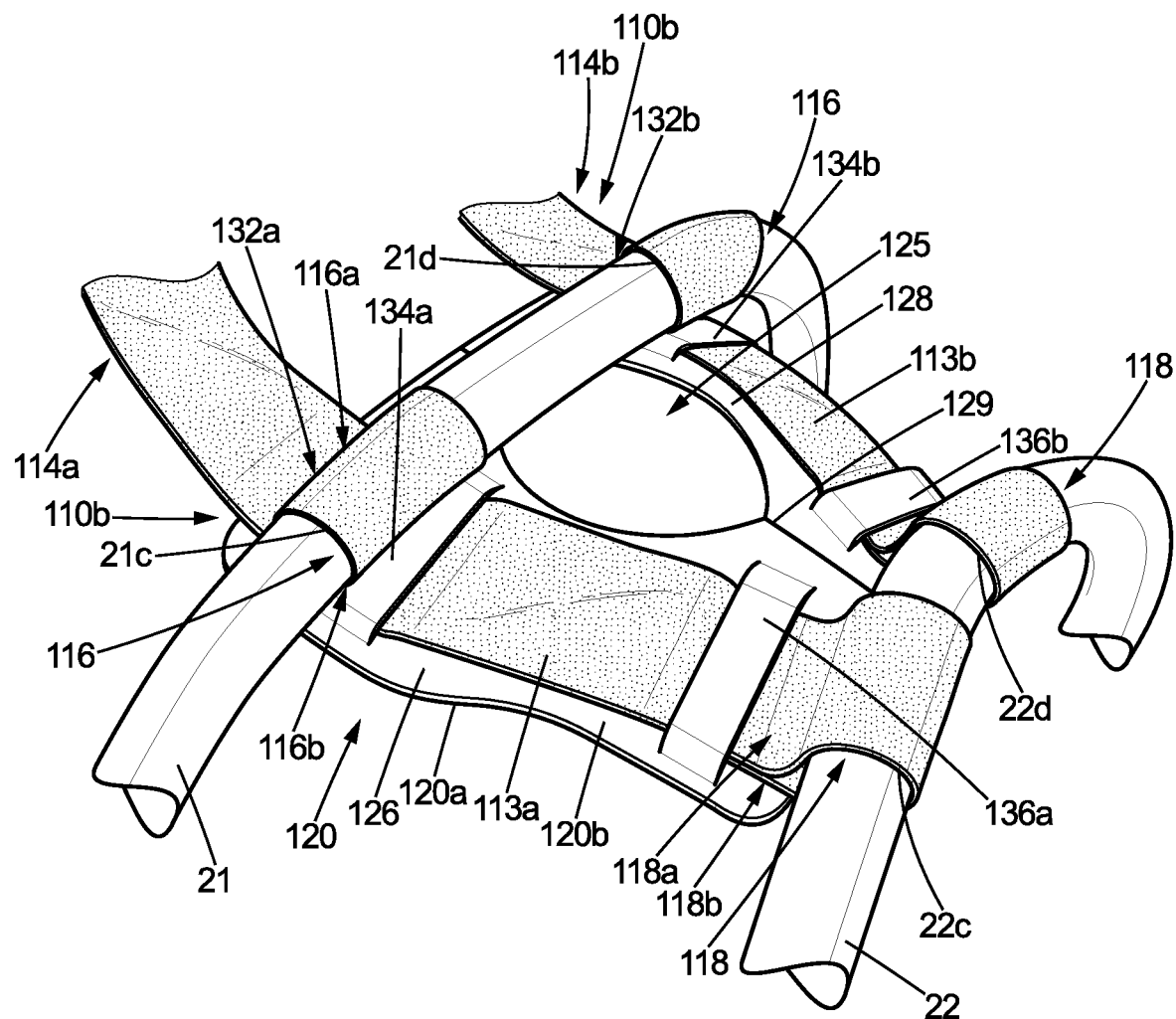
FIG. 4 depicts an enlarged view of a plate of the breathing apparatus according to a third alternative embodiment.

The alternative embodiment shown in FIG. 4 differs substantially from the alternative embodiment shown in FIG. 3 in that the first strap 113a and the second strap 113b extend beyond the lower end 110b, by each forming a proximal loop 116 and a distal loop 118, and the occipital plate 120 is not provided with the first upper holding member 121a, the first lower holding member 122a, the second upper holding member 121b and the second lower holding member 122b.

The proximal loop 116 of the first strap 113a and the second strap 113b extends between a first proximal end 116a and a second proximal end 116b around the first upper intermediate portion 21c and the second upper intermediate portion 21d, respectively, of the upper tube 21. The distal loop 118 of the first strap 113a and the second strap 113b extends between a first distal end 118a and a second distal end 118b around the first lower intermediate portion 22c and the second lower intermediate portion 22d, respectively, of the lower tube 22. The first distal end 118a and the second distal end 118b of the first strap 113a and the second strap are rigidly connected by sewing, welding or the like.

The first strap 113a and the second strap 113b pass alternately over the inner face 120a and the outer face 120b of the plate 120. The occipital plate 120 comprises a first upper keeper 132a, a first intermediate keeper 134a, a first lower keeper 136a, a second upper keeper 132b, a second intermediate keeper 134b, a second lower keeper 136b. The first strap 113a is in contact with the inner face 120a of the occipital plate 120 at the first upper keeper 132a, the first intermediate keeper 134a and the first lower keeper 136a. The first strap 113a is in contact with the outer face 120b of the occipital plate 120 on either side of the first upper keeper 132a, the first intermediate keeper 134a and the first lower keeper 136a, except that between the first upper keeper 132a and the first intermediate keeper 134a the upper tube 21 is positioned between the outer face 120b of the occipital plate 120 and the first strap 113a. The second strap 113b is in contact with the inner face 120a of the occipital plate 120 at the second upper keeper 132b, the second intermediate keeper 134b and the second lower keeper 136b. The second strap 113b is in contact with the outer face 120b of the occipital plate 120 on either side of the second upper keeper 132b, the second intermediate keeper 134b and the second lower keeper 136b, except that between the second upper keeper 132b and the second intermediate keeper 134b the upper tube 21 is positioned between the outer face 120b of the occipital plate 120 and the second strap 113b.

The first upper keeper 132a is located at the first proximal end 116a of the first strap 113a, the first intermediate keeper 134a is located at the second proximal end 116b of the first strap 113a and the first lower keeper 136a is located at the first distal end 118a and at the second distal end 118b of the first strap 113a. The second upper keeper 132b is located at the first proximal end 116a of the second strap 113b, the second intermediate keeper 134b is located at the second proximal end 116b of the second strap 113a and the second lower keeper 136b is located at the first distal end 118a and at the second distal end 118b of the second strap 113b.

Of course, the invention is by no means limited to the illustrative, non-limiting embodiment(s) described. Thus, the occipital plate 20 may be perforated, form a grid or the like, the occipital plate 20 essentially serving to prevent a portion of the harness 20 from being inserted into the first cavity 13 of the oronasal face cover 14 or the second cavity 15 of the support 17.

The invention claimed is:

1. A breathing apparatus for aircraft, the breathing apparatus being configured to supply a respiratory gas to a user and including:
  a breathing mask comprising a shell, the shell having a cavity and being configured for contacting the user's head around the user's mouth and nose, the shell supporting a transparent lens and comprising an upper edge portion extending above the transparent lens,
  an inflatable harness configured to extend around the user's head opposite the shell in order to hold the shell in contact with the user's face, the harness comprising at least one rear portion configured to be placed facing an occipital portion of the user's head,
  a guiding link having an upper end and a lower end, the upper end being linked to the upper edge portion, and
  a plate linked to the lower end of the guiding link and having a bearing face configured to contact the shell and to face the cavity, the plate being linked to the rear portion of the harness,
  wherein the guiding link has an upper portion and a lower portion, the upper portion being rigid and the guiding link being configured to be folded with the upper portion on the plate and the lower portion between the upper portion and the plate,
  wherein the upper portion has a length greater than or equal to 10 centimeters,
  wherein the upper portion is rotatably mounted on the upper edge portion, and
  wherein the lower portion is at least partly flexible and arranged between the upper portion and the plate.

2. The breathing apparatus according to claim 1, wherein the guiding link has a torsional flexibility of less than half a turn.

3. The breathing apparatus according to claim 1, wherein the guiding link has an elongate, flat shape.

4. The breathing apparatus according to claim 1, wherein the upper portion comprises two arms extending longitudinally and laterally separated from one another by a distance greater than or equal to 3 centimeters and the breathing apparatus comprises two lower portions extending between the upper portion and the plate.

5. The apparatus according to claim 1, wherein the lower portion comprises at least one rigid element.

6. The breathing apparatus according to claim 5, wherein the at least one rigid element comprises a series of rigid elements hingedly connected to one another.

7. The breathing apparatus according to claim 1, wherein the lower portion comprises a strap, the strap extending beyond the lower end forming a loop around a tube of the harness and the loop has ends held on the plate.

8. The breathing apparatus according to claim 1, wherein the lower end of the guiding link is linked to the rear portion of the harness via the plate.

9. The breathing apparatus according to claim 1, wherein the breathing apparatus is additionally provided with a sign for correct positioning in a stowage position.

10. The breathing apparatus according to claim 1, wherein the shell comprises an oronasal face cover and a support, the oronasal face cover having a first cavity and being configured to contact the user's head around the user's mouth and nose, the support supporting the transparent lens and having a second cavity.

11. A breathing unit comprising the breathing apparatus according to claim 1 and a stowage box wherein:
  the stowage box includes a housing configured to receive the breathing apparatus in a stowage position, said stowage box having an opening providing access to the housing.

12. A method for stowing the breathing apparatus of the breathing unit according to claim 11 in the stowage box wherein the method comprises:
  a) moving the plate to be in contact with the shell,
  b) pivoting the guiding link near the upper end of the guiding link with respect to the breathing mask,
  c) placing the breathing apparatus in a stowed position by folding the guiding link so that the upper portion of the guiding link, the lower portion of the guiding link and the plate overlap, and
  d) inserting the breathing apparatus into the stowage box.

* * * * *